United States Patent [19]

Makino et al.

[11] Patent Number: 5,501,861
[45] Date of Patent: Mar. 26, 1996

[54] FAST DISSOLVING TABLET AND ITS PRODUCTION

[75] Inventors: Tadashi Makino, Ibaraki; Masayuki Yamada, Kawanishi; Jun-ichi Kikuta, Suita, all of Japan

[73] Assignee: Takeda Chemical Industries, Ltd., Osaka, Japan

[21] Appl. No.: 301,036

[22] Filed: Sep. 6, 1994

Related U.S. Application Data

[63] Continuation of Ser. No. 10,398, Jan. 28, 1993, abandoned.

[30] Foreign Application Priority Data

Jan. 29, 1992 [JP] Japan ..................... 4-013511

[51] Int. Cl.$^6$ ..................... A61K 9/20
[52] U.S. Cl. ............ 424/464; 424/465; 424/468; 424/470; 424/489
[58] Field of Search ..................... 424/464, 465, 424/466

[56] References Cited

U.S. PATENT DOCUMENTS

| | | | |
|---|---|---|---|
| 2,926,121 | 2/1960 | Hobbs et al. | 167/82 |
| 4,414,198 | 11/1983 | Michaelson | 424/44 |
| 4,946,684 | 8/1990 | Blank et al. | 424/441 |
| 5,085,869 | 2/1992 | Olthoff | 424/499 |
| 5,112,616 | 5/1992 | McCarty | 424/464 |

FOREIGN PATENT DOCUMENTS

| | | |
|---|---|---|
| 0166440 | 1/1986 | European Pat. Off. . |
| 0192460 | 8/1986 | European Pat. Off. . |
| 0371466 | 6/1990 | European Pat. Off. . |
| 0450141 | 10/1991 | European Pat. Off. . |
| 6167M | 7/1968 | France . |
| 2335205 | 7/1977 | France . |
| 52-76420 | 6/1977 | Japan . |
| 58-24410 | 5/1983 | Japan . |
| 61-15830 | 1/1986 | Japan . |
| 1134097 | 11/1968 | United Kingdom . |
| 2111423 | 7/1983 | United Kingdom . |
| WO93/12769 | 7/1993 | WIPO . |

OTHER PUBLICATIONS

Zydis, Manufacturing Chemist, 1990, pp. 36–37.

*Primary Examiner*—Thurman K. Page
*Assistant Examiner*—William E. Benston, Jr.
*Attorney, Agent, or Firm*—Wenderoth, Lind & Ponack

[57] ABSTRACT

A method of producing a fast dissolving tablet comprising compression-molding a composition comprising an active ingredient, a carbohydrate and a barely sufficient amount of water to moisten the surface of particles of said carbohydrate into a tablet form and a fast dissolving tablet obtainable by the method. The active ingredient may, for example, be a vitamin, a gastrointestinal function conditioning agent or an antipyretic-analgesic-antiinflammatory agent. The carbohydrate includes sugar, starch sugars, lactose, honey, sugar alcohols and tetroses. The amount of water to be added is about 0.3 to 10% by weight. The above fast dissolving tablet has a porous structure with excellent disintegratability and solubility as well as adequate strength.

13 Claims, No Drawings

FAST DISSOLVING TABLET AND ITS PRODUCTION

This application is a continuation of now abandoned application Ser. No. 08/010,398, filed Jan. 28, 1993.

FIELD OF THE INVENTION

The present invention relates to a fast dissolving tablet comprising a pharmacologically active ingredient, such as a vitamin, antipyretic-analgesic-antiinflammatory agent, antihypertensive drug, psychotropic drug, antidiabetic drug or the like, and a carbohydrate, having an adequate strength and capable of dissolving and disintegrating at a high rate in the oral cavity and to a method of producing the tablet.

BACKGROUND OF THE INVENTION

Recently much research has been undertaken in the geriatric field ranging from the physiology of aging to the design of drugs and pharmaceutical preparations to daily care and assistance. According to, inter alia, the silver science research conducted by the Japanese Ministry of Health and Welfare, there is an interesting research report entitled 'Studies for the construction of new pharmaceutical preparations and new packaging containers optimal for administration to elderly subjects' (Masayasu Sugihara, Tokyo Women's Medical College, and others) (Aug. 22, 1989 issue of the Yakuji Nippo). By way of illustration, as such new preparations, a) buccal dissolution type preparations, b) paste-like preparations and c) jelly-like preparations are described. Particularly, buccal dissolution type and paste-like preparations are claimed to be easy for elderly persons to ingest and excellent in stability. The buccal dissolution type preparations, in particular, contain polyethylene glycol 1000 as the base which dissolves in the oral cavity and an oleaginous base as the base which melts at the temperature prevailing in the oral cavity and, in consideration of sensory factors such as taste and texture as well as moldability, further contain sucrose and mannitol. These are molded by filling the pocket of a vinyl chloride molding sheet for press-through package (PTP) use with a heat-melted medicated base and allowing it to cool and take form. In this manner, a buccal dissolution type solid preparation for elderly persons is manufactured.

Japanese Patent Laid-open No. 76420/1977 describes a method of manufacturing a porous tablet which features a high disintegration rate insuring rapid dissolution in the oral cavity which comprises placing a magmatic mixture or solution containing 5 to 80% by weight of an inert solvent freezing at a temperature of −30° C. to 25° C. and the balance of a tablet-forming composition in an inert cooling medium such as liquid nitrogen to cause solidification, then compressing the resulting granules into tablets at a temperature not higher than the freezing point of the solvent, and finally removing the solvent by freeze-drying or air drying.

Japanese Patent Publication No. 24410/1983 discloses a method of manufacturing a porous tablet with good disintegrability which comprises mixing a tablet-constituting composition with a solvent which is inert to said composition and freezes at a temperature of −30° to +25° C. (for example, water, cyclohexane or benzene), the proportion of said solvent being 5 to 80% by weight, placing the resulting mixture in an inert cooling medium for solidification, compressing the resulting solid into tablets at a temperature lower than the freezing point of said solvent and evaporating the solvent by freeze-drying or spontaneous drying.

Japanese Patent Laid-open No. 15830/1986 discloses an antacid composition having a porous and extra fine crystal structure which comprises an antacid and a base for confectionery comprising a sweetener for confectionery and a plasticizer.

On the other hand, in certain countries, there are guidelines (e.g. USA"FDA 1983) for research concerning pharmaceutical products for elderly persons and, as a buccal dissolution type solid preparation, Zydis from R. P. Scherer, England, is commercially available, for instance. While the composition of this preparation is not known, it is manufactured by blending an active ingredient with a polymer, sugar and other ingredients, dissolving the blend and freeze-drying the solution (Manuf. Chemist. Feb. 36, 1990).

However, from the standpoint of practical utility as buccal preparations, the conventional products described above are not fully satisfactory in shelf-life, solubility and the scope of compatible medicament. For Example, the composition described in said Japanese Patent Laid-open No. 15830/1986 is prepared by heating and melting the ingredients, so that it is inferior in the scope of compatible medicament and disintegratability of the preparation in the oral cavity. Also, Zydis (trade name) mentioned above has problems with the water solubility of the active ingredient, mechanical strength of the preparation, and % content of the active ingredient so that it is not satisfactory, either, for administration to patients of advanced age.

Furthermore, a tablet which disintegrates and dissolves quickly is generally weak in mechanical strength. Therefore, it has been considered necessary to develop a preparation which offers practically acceptable disintegration and dissolution speeds in the oral cavity and, at the same time, possesses a sufficient mechanical strength so that it will not be destroyed in the course of manufacture and subsequent distribution.

SUMMARY OF THE INVENTION

It is an object of the present invention to provide a fast dissolving tablet having adequate disintegratability and solubility in the oral cavity and sufficient mechanical strength to resist destruction in the course of manufacture and storage.

It is another object of the invention to provide a method of producing a fast dissolving tablet, by which a tablet having the above-mentioned desirable properties can be produced without requiring complicated production procedures.

It is a further object of the invention to provide a fast dissolving tablet which is easy for elderly per sons and children to ingest and is, therefore, practically useful and a method of producing the tablet.

Under the circumstances described above, the inventors of the present invention found, after much research for designing a buccal dissolution type pharmaceutical preparation, that when a mixture comprising a pharmacologically active ingredient, a carbohydrate and a barely sufficient amount of water to moisten the surface of particles of the carbohydrate is compression-molded and afterwards dried, there is surprisingly obtained a porous tablet having sufficient mechanical strength resisting destruction in the course of manufacture, storage and distribution and yet capable of disintegrating and dissolving rapidly in the oral cavity without resort to complex production steps which are usually required, such as heating, melting, dissolving, freezing, etc. and that this tablet is fully suitable for use as a buccal dissolution type tablet. The present invention has been brought into being on the basis of the above findings.

The fast dissolving tablet of the present invention can be manufactured by compression-molding a composition comprising a pharmacologically active ingredient, a carbohydrate and a barely sufficient amount of water to wet the surface of particles of said carbohydrate into a tablet form.

Said fast dissolving tablet can be suitably utilized as a buccal dissoluble and disintegratable tablet because of its easy solubility and disintegratability in the oral cavity.

As the pharmacologically active ingredient, there may be mentioned vitamins, crude drugs, antipyretic-analgesic-antiinflammatory agents, antianxiety drugs, hypnotic-sedative agents, gastrointestinal function conditioning agents, antitussive-expectorants, antihypertensive drugs, antidiabetic agents, drugs for osteoporosis, skeletal muscle relaxants and so on. The proper proportion of the pharmacologically active ingredient in said composition is approximately 0.05 to 90% by weight.

The carbohydrate which can be used includes sucrose, starch sugars, sugar alcohols, tetroses and so on. The carbohydrate content of said composition may, for example, range from about 10 to 90% by weight.

The pressure for compression-molding may, for example, range from about 3 to 160 Kg/cm$^2$.

The fast dissolving tablet of the present invention has a porous structure with a porosity of about 20 to 80%.

DETAILED DESCRIPTION OF THE INVENTION

The pharmacologically active ingredient for use in the present invention may be in any optional form, for example, a solid, particulate, granular, crystalline, or oily or solution form. The active ingredient may be at least one member selected from the group consisting of nourishing and health-promoting agents, antipyretic-analgesic-inflammatory agents, antipsychotic drugs, antianxiety drugs, antidepressants, hypnotic-sedative agents, spasmolytics, gastrointestinal function conditioning agents, antacids, antitussive-expectorants, dental buccal drugs, antihistamines, cardiotonics, antiarrhythmic drugs, diuretics, antihypertensive drugs, vasoconstrictors, coronary vasodilators, peripheral vasodilators, cholagogues, antibiotics, chemotherapeutic drugs, antidiabetic agents, drugs for osteoporosis, skeletal muscle relaxants and so on.

Among said nourishing and health-promoting agents are various vitamins such as vitamin A, vitamin D, vitamin E (d-α-tocopherol acetate, etc.), vitamin $B_1$ (dibenzoylthiamin, fursultiamine hydrochloride, etc.), vitamin $B_2$ (riboflavin butyrate, etc.), vitamin $B_6$ (pyridoxine hydrochloride, etc.), vitamin C (ascorbic acid, sodium L-ascorbate, etc.), vitamin B12 (hydroxocobalamin acetate, etc.); minerals such as calcium, magnesium, iron; proteins; amino acids; oligosaccharides and crude drugs.

Among said antipyretic-analgesic-antiinflammatory agents are aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, serratiopeptidase, lysozyme chloride, tolfenamic acid, mefenamic acid, diclofenac sodium, flufenamic acid, salicylamide, aminopyrine, ketoprofen, indomethacin, bucolome, pentazocine and so on.

Among said antipsychotic drugs are chlorpromazine, reserpine and so on. The antianxiety drugs include chlordiazepoxide, diazepam and so on. The antidepressants include imipramine, maprotiline, amphetamine and so on. Among said hipnotic-sedatives are estazolam, nitrazepam, diazepam, phenobarbital sodium and so on. The spasmolytics include scopolamine hydrobromide, di-phenhydramine hydrochloride, papaverine hydrochloride and so on.

The gastrointestinal function conditioning agents include stomachic-digestives such as diastase, saccharated pepsin, scopolia extract, lipase AP, cinnamon oil, etc. and intestinal function controlling drugs such as berberine chloride, resistant lactic acid bacterium, Lactobacillus bifidus and so on. As said antacids, there may be mentioned magnesium carbonate, sodium hydrogen carbonate, magnesium aluminometasilicate, synthetic hydrotalcite, precipitated calcium carbonate, magnesium oxide and so on.

The antitussive-expectorants include chloperastine hydrochloride, dextromethorphan hydrobromide, theophylline, potassium guaiacolsulfonate, guaifenesin and so on. The dental buccal drugs include oxytetracycline, triamcinolone acetonide, chlorhexidine hydrochloride, lidocaine and so on.

The antihistamines include diphenhydramine hydrochloride, promethazine, isothipendyl hydrochloride, dl-chlorpheniramine maleate and so on.

The cardiotonics include etilefrine hydrochloride and so on. The antiarrhythmic drugs include procainamide hydrochloride, propranolol hydrochloride, pindolol and so on. The diuretics include isosorbide, furosemide and so on. The antihypertensive drugs include delapril hydrochloride, captopril, hexamethonium bromide, hydralazine hydrochloride, labetalol hydrochloride, methyldopa and so on.

The vasoconstrictors include phenylephrine hydrochloride etc. The coronary vasodilators include carbocromen hydrochloride, molsidomine, verapamil hydrochloride and so on. The peripheral vasodilators include cinnarizine and so on. The cholagogues include dehydrocholic acid, trepibutone and so on.

The antibiotics include cephems, penems and carbapenems such as cefalexin, amoxicillin, pivmecillinam hydrochloride, cefotiam dihydrochloride and so on. The chemotherapeutic drugs include sulfamethizole, thiazosulfone and so on. The antidiabetic agents include tolbutamide, voglibose and so on. The drugs for osteoporosis include ipriflavone and so on. The skeletal muscle relaxants include methocarvamol and so on.

The active ingredient may have been diluted with a diluent which is used generally in the pharmaceutical or food industry. At least one of active ingredients may be oily.

Preferred examples of such active ingredient for purposes of the present invention are the vitamins, crude drugs, antipyretic-analgesic-antiinflammatory agents, antianxiety drugs, hypnotic-sedative agents, gastrointestinal function conditioning agents, antitussive-expectorants, antihypertensive drugs, antidiabetic agents, drugs for osteoporosis, skeletal muscle relaxants mentioned hereinbefore.

The recommendable proportion of the active ingredient in the composition comprising it, a carbohydrate and water is dependent on its type but is generally about 0.05 to 90% by weight and preferably 0.1 to 70% by weight and more preferably 0.3 to 60% by weight.

The carbohydrate for use in the present invention may be any carbohydrate that is soluble in water and does not adversely affect the active ingredient (for example, decomposition of the active ingredient). Thus, for example, sugar, starch sugars, lactose, honey, sugar alcohols, tetroses, etc. can be employed.

The sugar includes, among others, sucrose, coupling sugar, fructoligosaccharides, palatinose and so on. The starch sugars include, among others, glucose, maltose, powdered syrup, starch syrup, isomerized sugar (fructose) and so on. The lactose includes, among others, lactose, isomerized lactose (lactulose), reduced lactose (lactitol) and so on. The honey may be any of the various types which are commonly used as food. The sugar alcohol includes, among others, sorbitol, mannitol, reduced malt syrup (maltitol), reduced starch saccharides, xylitol, reduced palatinose and so on. Tetroses obtainable by fermentation of glucose (e.g. erythritol) can also be employed. These carbohydrates can be used independently or in combination.

The preferred species of carbohydrate for purposes of the present invention are sucrose, glucose, -malti tol, xylitol, erythritol and so on.

Mean particle size of the carbohydrate is usually in the range of 1 to 100 μm, preferably 20 to 70 μm and more preferably 30 to 50 μm.

The proportion of the carbohydrate in the above composition varies with the type of active ingredient but generally speaking may be about 10 to 90% by weight, preferably about 20 to 85% by weight and, for still better results, about 30 to 80% by weight.

In the case where the proportion of the active ingredient is in the range of 0.1 to 10% by weight in the composition, where the dosage of the active ingredient is small, the proportion of the carbohydrate in the composition is generally in the range of 30 to 90% by weight, preferably 50 to 85% by weight and more preferably 60 to 85% by weight. As examples of the active ingredient whose dosage is small, there may be mentioned diazepam and the like.

In the case where the proportion of the active ingredient is in the range of 10 to 30% by weight in the composition, where the dosage of the active ingredient is moderate, the proportion of the carbohydrate in the composition is generally 20 to 90% by weight, preferably 30 to 80% by weight and more preferably 40 to 75% by weight. As examples of the active ingredient whose dosage is moderate, there may be mentioned antipyretic-analgesic-inflammatory agents and the like.

In the case where the proportion of the active ingredient is in the range of 30 to 70% by weight in the composition, where the dosage of the active ingredient is large, the proportion of the carbohydrate in the composition is usually 10 to 70% by weight, preferably 15 to 60% by weight and more preferably 20 to 50% by weight. As examples of the active ingredient whose dosage is large, there may be mentioned vitamin C and the like.

Unless the object of the invention is interfered with, the above-mentioned composition may further contain a variety of additives which are commonly employed in the manufacture of tablets.

The additives mentioned above include, among others, disintegrators, binders, acids, foaming agents, artificial sweeteners, flavorants, lubricants, colorants and so on.

The disintegrators include, among others, corn starch, potato and other starches, carmellose calcium, carmellose sodium and polyvinyl alcohol. The binders include, among others, gum arabic powder, gelatin and pullulan.

The acids include but are not limited to citric acid, tartaric acid and malic acid. The foaming agents include sodium hydrogen carbonate and so on. The artificial sweeteners include saccharin sodium, dipotassium glycyrrhizinate, aspartame, stevia, thaumatin and so on.

The flavorants include but are not limited to lemon, lime, orange and menthol. The lubricants include, among others, magnesium stearate, sucrose fatty acid ester, polyethylene glycols, talc and stearic acid. The colorants include, among others, various food colors such as FD&C Yellow No. 6, FD&C Red No. 2, FD&C Blue No. 2, etc., food lakes, red iron oxide and so on.

One or more of these additives can be added in appropriate proportions, for example at the blending of the active ingredient with the carbohydrate, at addition of water, in the course of kneading or before and after any of such stages.

The amount of water in said composition may be a barely sufficient. amount to moisten the surface of particles of said carbohydrate. In the present invention, the surfaces of the carbohydrates are particles wetted, so that particles of the carbohydrate adhere to each other mainly at the surface of said particles to give a porous tablet having adequate porosity and hardness to buccal tablet by compression-modling.

The proper amount of water, which depends on the types and amounts of active ingredient, carbohydrate and additives, may be generally 0.3 to 10% by weight, preferably 0.3 to 7% by weight, more preferably 0.5 to 3% by weight, for still better results, about 0.7 to 3% by weight and most preferably 1 to 3% by weight based on the weight of the above composition. If the amount of water is too small, the mechanical (falling impact) strength of tablets will not be sufficiently high, while the use of an excessive amount of water tends to cause adhesion of the active ingredient and others to the molding equipment (for example, the punch and die cavity), thus interfering with molding.

To be specific, when the composition contains 20 to 40% by weight of xylitol and/or maltitol as the carbohydrate, water is added in a proportion of generally 0.5 to 5.0% by weight and preferably 1.0 to 2.0% by weight relative to the composition. When the composition contains 60 to 80% by weight of sucrose and/or glucose as the carbohydrate, water is added generally in a proportion of 1.5 to 2.5% by weight relative to the composition. Furthermore, when the composition contains 55 to 75% by weight of erythritol as the carbohydrate, water is generally added in a proportion of 1.5 to 2.5% by weight.

The amount of water may be controlled by adding water to an optional ingredient or mixture thereof, and the addition method of water is not limited; water may be added at once, drop by drop or by spraying.

For example, to a blended mixture of the active ingredient with the carbohydrate and, if necessary, said additives, may be added a barely sufficient amount of water to moisten the surface of carbohydrate particles in said mixture.

The blending of the above ingredients can be carried out by any of the conventional blending techniques such as mixing, kneading, sieving and so on. Specifically, Vertical Granulator GV10 (Powrex), Universal Kneader (Hata Iron Works, Ltd.), fluidized bed granulator FD-5S (Powrex) and Gyrosifter (Tokuju Seisakusho), for instance, can be employed.

The composition comprising an active ingredient, a carbohydrate and water is usually kneaded before making tablets.

The kneading operation of the composition containing water can be carried out by the routine method commonly used in the art. For example, the devices mentioned hereinbefore for the blending of the ingredients can be utilized.

The molding of tablets can be carried out using the equipment commonly used in the granulation and compression-molding of tablets. For example, a single-punch tablet machine (Kikusui Seisakusho) or a rotary tablet machine (Kikusui Seisakusho) can be employed. The molding pressure is generally about 3 to 160 $Kg/cm^2$, preferably about 5 to 130 $Kg/cm^2$ and for still better results, about 8 to 50 $Kg/cm^2$. The molding temperature is such a temperature that particles of the carbohydrate are not dissolved nor melted, and is generally ambient temperature (20° to 30° C., for instance) and preferably about 25° C.

The tablets thus molded are preferably dried. The drying operation can be carried out by any of the techniques used commonly in the art, such as vacuum drying, freeze drying, spontaneous drying and so on.

These tablets can be coated to the extent not adversely affecting the hardness or solubility of the tablets by any coating method that is generally used in the manufacture of coated tablets.

The fast dissolving tablet thus obtained has a porous structure. The term 'porous structure' is used herein to mean a tablet having a porosity of generally 20 to 80% and preferably 30 to 70%. This porous tablet is excellent in disintegratability and solubility in the oral cavity and has a high falling impact strength.

Thus, the tablet of the invention has a buccal solubility (a time to complete dissolution by saliva in the oral cavity in a healthy adult male) of generally 0.05 to 3.0 minutes and preferably 0.1 to 1.5 minutes, a disintegration time (a time measured by the disintegration test described in Japanese Pharmacopoeia XII) of generally 0.05 to 3.0 minutes and preferably 0.1 to 1.5 minutes, a hardness (a value measured with tablet hardness tester) of generally 2 to 25 kg and preferably 3 to 20 kg, and a falling impact strength (a degree of destruction when the tablet is dropped from a height of 30 cm on a glass plate) of generally 0 to 70% and prefeably 0 to 40%.

Therefore, the fast dissolving tablet of the present invention can be used for the therapy or prophylaxis of various diseases just as the conventional preparations containing the same active ingredient but with an increased ease of ingestion by elderly persons and children and also as safe preparations for general adults. The tablet of the invention further features a long shelf-life.

The fast dissolving tablet of the present invention contains the active ingredient in a proportion of generally about 0.05 to 90% by weight, preferably about 0.1 to 70% by weight, more preferably 0.3 to 60% by weight and the carbohydrate in a proportion of generally about 10 to 90% by weight, preferably about 20 to 85% by weight and, for still better results, about 30 to 80% by weight.

In the case where the dosage of the active ingredient is small, the tablet of the invention contains the active ingredient in a proportion of generally about 0.1 to 10% by weight, and the carbohydrate in a proportion of generally 30 to 90% by weight, preferably 50 to 85% by weight and more preferably 60 to 85% by weight.

In the case where the dosage of the active ingredient is moderate, the tablet of the invention contains the active ingredient in a proportion of generally about 10 to 30% by weight, and the carbohydrate in a proportion of generally 20 to 90% by weight, prefeably 30 to 80% by weight and more preferably 40 to 75% by weight.

In the case where the dosage of the active ingredient is large, the tablet of the invention contains the active ingredient in a proportion of generally about 30 to 70% by weight, and the carbohydrate in a proportion of generally 10 to 70% by weight, preferably 15 to 60% by weight and more preferably 20 to 50% by weight.

The fast dissolving tablet of the invention can be dosed just as the conventional oral preparations containing the same active ingredient. The dosage of the tablet of the invention varies according to the type of active ingredient and the patient's age, sex and condition, among other factors. For example, in the case where the active ingredeint is diazepam, the tablet is generally administered to adults such that a daily dosage of the active ingredient is in the range of about 0.01 to 100 mg, preferably 0.1 to 30 mg, and for still better results, 0.3 to 10 mg once a day or in 2 or 3 divided doses. Also, when the vitamin C-containing tablet of the invention is administered as a nourishing and health promoting drug, the dosage of the tablet is about 2 to 2000 mg/day and preferably about 100 to 2000 mg/day as vitamin C.

The fast dissolving tablet of the invention is easy to ingest because it is readily disintegratable and soluble in the oral cavity and has a long shelf life because it has adequate mechanical strength. Therefore, the tablet can be advantageously used for the prevention or treatment of diseases in patients, particularly aged and pediatric patients.

In accordance with the manufacturing method of the invention, the easily disintegratable troche having the above-mentioned excellent characteristics can be easily manufactured without resort to complicated procedures.

The following examples are further illustrative but by no means limitative of the present invention.

Examples

Reference Example 1

A granulating machine (Vertical Granulator VG10, Powrex) was charged with ascorbic acid, riboflavin buty-rate, d-α-tocopherol, xylitol, maltitol, corn starch, aspartame and powdered acacia in the amounts indicated in Table 1 and the charge was stirred for 1 minute. Then, 200 ml of water was added and the mixture was kneaded. The kneaded mass was dried in vacuo using a box type vacuum dryer (Kusuki Seisakusho) and comminuted with a sifting granulator (Powermill, Showa Chemical Machinery). After addition of magnesium stearate (0.5%), the granules were blended in a tumbler mixer (Showa Chemical Machinery) for 3 minutes. Using a single-punch tablet machine (Kikusui Seisakusho), the above granules were compression-molded with a flat punch having a beveled edge, 20 mm in diameter, at a molding pressure of 1910 $Kg/cm^2$ (force: 6000 Kg) to provide about 900 tablets.

Reference Example 2

A kneader (Universal Blender, Hata Iron Works) was charged with diazepam, sucrose, glucose, potato starch, citric acid, gelatin and FD&C Yellow No. 6 in the amounts indicated in Table 2 and the charge was blended for 2 minutes. Then, 50 ml of alcohol and 50 ml of water were added and the mixture was kneaded. The kneaded mass was dried in vacuo using a box type vacuum dryer (Kusuki Seisakusho) and comminuted with a cutter mill (Fitzmill, Hosokawa Micron). After Addition of sucrose fatty acid ester (0.5%), the granules were mixed with a mixer (V Mixer, Patterson-Kelly) for 1 minute. Then, using a rotary tablet machine (Correct 19K, Kikusui Seisakusho), the granules were compression-molded with a flat punch having a beveled edge, 15 mm in diameter, at a molding pressure of 1980 $Kg/cm^2$ (force: 3500 Kg) to provide about 900 tablets.

Reference Example 3

A fluidized-bed granulator (FD-5S, Powrex) was charged with ibuprofen, caffeine, erythritol, citric acid, carmellose calcium, corn starch, stevia and menthol in the amounts indicated in Table 3 and the charge was mixed for 3 minutes. Then, 120 ml of water was sprayed and the mixture was further granulated. The granules were dried and comminuted with a cutter mill (Power Mill, Showa Chemical Machinery). To the granules were added 0.2% of magnesium stearate and 1.8% of talc and the mixture was blended with a mixer (Tumbler Mixer, Showa Chemical Machinery) for 3 minutes. Then, the granules were compression-molded with a rotary tablet machine (Correct 19K, Kikusui Seisakusho) with a flat punch having a beveled edge, 15 mm in diameter, at a molding pressure of 1700 Kg/cm$^2$ (force: 3000 Kg) to provide about 900 tablets.

Reference Example 4

The procedure of Reference Example 1 was repeated except that water was added in an amount of 40 ml (2%) and a compression molding pressure of 32 Kg/cm$^2$ (force: 100 Kg) was used to provide about 900 tablets.

Example 1

A granulating machine (Vertical Granulator VG10, Powrex) was charged with ascorbic acid, riboflavin buty-rate, d-α-tocopherol, xylitol, maltitol, corn starch, aspartame and powdered acacia in the amounts indicated in Table 1 and the charge was mixed for 1 minute. Then, 32 ml of water was added and the mixture was kneaded. Using a single-punch tablet machine (Kikusui Seisakusho), the mixture was compression-molded with a flat punch having a beveled edge, 20 mm in diameter, at a molding pressure of 32 Kg/cm$^2$ (force: 100 Kg) to provide about 800 tablets. The tablets were dried in vacuo using a box type vacuum dryer (Kusuki Seisakusho).

TABLE 1

| Ingredient | Formula Amount added (g) |
|---|---|
| Ascorbic acid | 370 |
| Sodium ascorbate | 420 |
| Riboflavin butyrate | 2.2 |
| d-α-Tocopherol | 112 |
| Xylitol | 600 |
| Maltitol | 100 |
| Corn starch | 383.8 |
| Aspartame | 2 |
| Powdered acacia | 10 |
| Total | 2000 |

Example 2

A kneader (Universal Kneader, Hata Iron Works) was charged with diazepam, sucrose, glucose, potato starch, citric acid, gelatin and FD&C Yellow No. 6 in the amounts indicated in Table 2 and the charge was mixed for 2 minutes. Then, 10 ml of alcohol and 10 ml of water were added and the mixture was kneaded. Using a tablet machine (single-punch tablet machine, Kikusui Seisakusho), the mixture was compression-molded with a punch having a concave surface, 10 mm in diameter, at a molding pressure of 38 Kg/cm$^2$ (force: 30 Kg) to provide about 800 tablets. The tablets were dried in vacuo using a box type vacuum dryer (Kusuki Seisakusho).

TABLE 2

| Ingredient | Formula Amount added (g) |
|---|---|
| Diazepam | 1 |
| Sucrose | 271.45 |
| Glucose | 100 |
| Potato starch | 100 |
| Citric acid | 25 |
| Gelatin | 2.5 |
| FD & C Yellow No. 6 | 0.05 |
| Total | 500 |

Example 3

A fluidized bed granulator (FD-SS, Powrex) was charged with ibuprofen, caffeine, erythritol, citric acid, carmellose calcium, corn starch, stevia and menthol in the amounts indicated in Table 3 and the charge was mixed for 3 minutes. The mixture was granulated while 20 ml of water was sprayed and the resulting granules were compression-molded with a flat punch having a rounded edge, 15 mm in diameter, at a molding pressure of 34 Kg/cm$^2$ (force: 60 Kg) to provide about 800 tablets. The tablets were air-dried in a mini-jet oven (Toyama Sangyo).

TABLE 3

| Ingredient | Formula Amount added (g) |
|---|---|
| Ibuprofen | 100 |
| Caffeine | 12.5 |
| Erythritol | 655.5 |
| Citric acid | 100 |
| Carmellose calcium | 30 |
| Corn starch | 100 |
| Stevia | 1 |
| Menthol | 1 |
| Total | 1000 |

Example 4

Except that the molding pressure was 10 Kg/cm$^2$ (force: 30 Kg), the procedure of Example 1 was otherwise repeated to provide about 800 tablets.

Example 5

Except that the kneading operation was carried out using 10 ml of water, the procedure of Example 1 was repeated to provide about 800 tablets.

Example 6

Except that the amount of water was 100 ml, the procedure of Example 1 was repeated to provide about 800 tablets.

Example 7

Except that the ingredients indicated in Table 4 and 36 ml of water were used, the procedure of Example 1 was repeated to provide about 800 tablets.

TABLE 4

| Ingredient | Amount added (g) |
|---|---|
| Ascorbic acid | 303 |
| Sodium L-ascorbate | 409 |
| Riboflavin butyrate | 2 |
| d-α-Tocopherol acetate | 100 |
| Pyridoxine hydrochloride | 15 |
| Xylitol | 475 |
| Sucrose | 234 |
| Maltitol | 50 |
| Potato starch | 400 |
| Powdered acacia | 10 |
| Aspartame | 2 |
| Total | 2000 |

Formula

Example 8

Except that the ingredients indicated in Table 5 and 40 ml of water were used and the molding pressure was 36 Kg/cm$^2$ (force: 110 Kg), the procedure of Example 1 was repeated to provide about 800 tablets.

TABLE 5

| Ingredient | Amount added (g) |
|---|---|
| Acetaminophen | 300 |
| Ethenzamide | 450 |
| Anhydrous caffeine | 50 |
| Xylitol | 405 |
| Sucrose | 233 |
| Maltitol | 50 |
| Corn starch | 500 |
| Macrogol 6000 | 20 |
| Powdered acacia | 10 |
| Aspartame | 2 |
| Total | 2020 |

Formula

Example 9

Except that the ingredients indicated in Table 6 and 9 ml of water were used and the molding pressure was 101 Kg/cm$^2$ (force: 80 Kg), the procedure of Example 2 was repeated to provide about 1600 tablets.

TABLE 6

| Ingredient | Amount added (g) |
|---|---|
| Dimenhydrinate | 50 |
| Scopolamine hydrobromide | 0.1 |
| Caffeine | 30 |
| Sucrose | 709.9 |
| Corn starch | 100 |
| Potato starch | 100 |
| Powdered acacia | 10 |
| Total | 1000 |

Formula

Example 10

Except that the ingredients indicated in Table 7 and 11 ml of water were used and the molding pressure was 127 Kg/cm$^2$ (force: 100 Kg), the procedure of Example 2 was repeated to provide about 1600 tablets.

TABLE 7

| Ingredient | Amount added (g) |
|---|---|
| Idebenone | 30 |
| Xylitol | 500 |
| Sucrose | 215 |
| Potato starch | 250 |
| Gelatin | 5 |
| Total | 1000 |

Formula

Example 11

Except that the ingredients indicated in Table 8 and 28 ml of water were used and the molding pressure was 38 Kg/cm$^2$ (force: 120 Kg), the procedure of Example 1 was repeated to provide about 800 tablets.

TABLE 8

| Ingredient | Amount added (g) |
|---|---|
| Acetaminophen | 300 |
| Chlorpheniramine maleate | 2.5 |
| Dihydrocodein phosphate | 8 |
| Noscapine | 16 |
| dl-Methylephedrine hydrochloride | 20 |
| Serratiopeptidase | 5 |
| Anhydrous caffeine | 25 |
| Kumulite ® | 90 |
| Xylitol | 800 |
| Glucose | 418.5 |
| Corn starch | 300 |
| Powdered acacia | 10 |
| Aspartame | 5 |
| Total | 2000 |

Formula

Example 12

Except that the ingredients indicated in Table 9 and 24 ml of water were used and the molding pressure was 35 Kg/cm$^2$ (force: 110 Kg), the procedure of Example 1 was repeated to provide about 800 tablets.

TABLE 9

| Ingredient | Amount added (g) |
|---|---|
| Acetaminophen | 300 |
| Chlorpheniramine maleate | 2.5 |
| Dihydrocodein phosphate | 8 |
| Noscapine | 16 |
| dl-Methylephedrine hydrochloride | 20 |
| Serratiopeptidase | 5 |
| Guaifenesin | 83 |
| Ascorbic acid | 100 |
| Anhydrous caffeine | 25 |
| Sucrose | 628 |
| Erythritol | 600 |
| Potato starch | 200 |
| Powdered acacia | 10 |
| Saccharin sodium | 2.5 |
| Total | 2000 |

Formula

Example 13

Except that the ingredients indicated in Table 10 and 20 ml of water were used and the molding pressure was 29 Kg/cm² (force: 90 Kg), the procedure of Example 1 was repeated to provide about 800 tablets.

TABLE 10

| Formula | |
|---|---|
| Ingredient | Amount added (g) |
| Methocarvamol | 500 |
| Ethenzamide | 300 |
| Anhydrous caffeine | 30 |
| Tocopherol acetate | 30 |
| Dibenzoylthiamin | 8 |
| Maltitol | 500 |
| Xylitol | 312 |
| Corn starch | 300 |
| Gelatin | 10 |
| Menthol | 5 |
| Aspartame | 5 |
| Total | 2000 |

Example 14

Except that the ingredients indicated in Table 11 and 24 ml of water were used, the procedure of Example 1 was repeated to provide about 800 tablets.

TABLE 11

| Formula | |
|---|---|
| Ingredient | Amount added (g) |
| Tochu extracts | 30 |
| Ginseng extracts | 100 |
| Rokuzyo | 5 |
| Vitamin A | 1 × 10⁶ IU |
| Ascorbinic acid | 125 |
| d-α-Tocopherol acetate | 5 |
| Fursulthiamin hydrochloride | 5 |
| Riboflavin butyrate | 5 |
| Pyridoxine hydrochloride | 12.5 |
| Hydroxocobalamin acetate | 30 × 10⁻³ |
| Dibasic calcium phosphate | 20 |
| Precipitated calcium carbonate | 62 |
| Sucrose | 1305 |
| Potato starch | 300 |
| Powdered acacia | 10 |
| Aspartame | 10 |
| Lemon oil | 5 |
| Total | 2000 |

Example 15

Except that the ingredients indicated in Table 12 and 30 ml of water were used and the molding pressure was 30 Kg/cm² (force: 90 Kg), the procedure of Example 1 was repeated to provide about 800 tablets.

TABLE 12

| Formula | |
|---|---|
| Ingredient | Amount added (g) |
| Daiôkanzôtô extract powder | 400 |
| Xylitol | 800 |
| Sucrose | 440 |
| Potato starch | 150 |

TABLE 12-continued

| Formula | |
|---|---|
| Ingredient | Amount added (g) |
| Corn starch | 200 |
| Powdered acacia | 10 |
| Total | 2000 |

Example 16

Except that the ingredients indicated in Table 13 and 30 ml of water were used, the procedure of Example 1 was repeated to provide about 800 tablets.

TABLE 13

| Formula | |
|---|---|
| Ingredient | Amount added (g) |
| Ascorbic acid | 500 |
| Sodium L-ascorbate | 560 |
| Riboflavin butyrate | 3 |
| Sucrose | 512 |
| Corn starch | 400 |
| Aspartame | 5 |
| Powdered acacia | 15 |
| Lemon oil | 5 |
| Total | 2000 |

Example 17

Except that the ingredients indicated in Table 14 and 40 ml of water were used and the molding pressure was 29 Kg/cm² (force: 90 Kg), the procedure of Example 1 was repeated to provide about 800 tablets.

TABLE 14

| Formula | |
|---|---|
| Ingredient | Amount added (g) |
| Kôshaheiisankashakuyaku | 700 |
| Sucrose | 985 |
| Corn starch | 300 |
| Powdered acacia | 10 |
| Aspartame | 5 |
| Total | 2000 |

Example 18

Except that the ingredients indicated in Table 15 and 24 ml of water were used and the molding pressure was 25 Kg/cm² (force: 80 Kg), the procedure of Example 1 was repeated to provide about 800 tablets.

TABLE 15

| Formula | |
|---|---|
| Ingredient | Amount added (g) |
| Antyusan | 500 |
| Sorbitol | 700 |
| Sucrose | 485 |
| Potato starch | 300 |
| Aspartame | 5 |

Example 19

Except that the ingredients indicated in Table 16 and 10 ml of water were used and the molding pressure was 25 Kg/cm$^2$ (force: 80 Kg), the procedure of Example 1 was repeated to provide about 400 tablets.

TABLE 15-continued

| Ingredient | Formula Amount added (g) |
|---|---|
| Powdered acacia | 10 |
| Total | 2000 |

TABLE 16

| Ingredient | Formula Amount added (g) |
|---|---|
| Ipriflavon | 200 |
| Xylitol | 645 |
| Potato starch | 150 |
| Gelatin | 5 |
| Total | 1000 |

Example 20

Except that the ingredients indicated in Table 17 and 16 ml of water were used, the procedure of Example 1 was repeated to provide about 800 tablets.

TABLE 17

| Ingredient | Formula Amount added (g) |
|---|---|
| Methyldopa | 500 |
| Xylitol | 800 |
| Sucrose | 280 |
| Corn starch | 400 |
| Macrogol 6000 | 10 |
| Powdered acacia | 15 |
| Aspartame | 5 |
| Total | 2010 |

Example 21

Except that the ingredients indicated in Table 18 and 24 ml of water were used and the molding pressure was 25 Kg/cm$^2$ (force: 80 Kg), the procedure of Example 1 was repeated to provide about 800 tablets.

TABLE 18

| Ingredient | Formula Amount added (g) |
|---|---|
| Tolbutamide | 500 |
| Xylitol | 1090 |
| Potato starch | 400 |
| Powdered acacia | 10 |
| Total | 2000 |

Example 22

Except that the ingredients indicated in Table 19 and 6 ml of alcohol and 6 ml of water were used and the mixture was compression-molded with a punch of 9 mm in diameter at a molding pressure of 31 Kg/cm$^2$ (force: 20 Kg), the procedure of Example 2 was repeated to provide about 1000 tablets of 300 mg.

TABLE 19

| Ingredient | Formula Amount added (g) |
|---|---|
| Diazepam | 1 |
| Xylitol | 160 |
| Sucrose | 78 |
| Potato starch | 60 |
| Powdered acacia | 1 |
| Total | 300 |

Example 23

Except that the ingredients indicated in Table 20 were used, the procedure of Example 22 was repeated to provide about 1000 tablets of 300 mg.

TABLE 20

| Ingredient | Formula Amount added (g) |
|---|---|
| Diazepam | 10 |
| Xylitol | 160 |
| Sucrose | 68 |
| Potato starch | 60 |
| Powdered acacia | 1 |
| Total | 300 |

Example 24

Except that the ingredients indicated in Table 21 were used, the procedure of Example 22 was repeated to provide about 1000 tablets of 300 mg.

TABLE 21

| Ingredient | Formula Amount added (g) |
|---|---|
| Diazepam | 20 |
| Xylitol | 160 |
| Sucrose | 58 |
| Potato starch | 60 |
| Powdered acacia | 1 |
| Total | 300 |

Test Examples

To illustrate the effects of the invention in further detail, the following characteristics of the tablets prepared in the foregoing Examples were determined. The results are shown in Table 22. Similar determinations were also made with the control tablets prepared in Reference Examples. The results are shown in Table 23.

(1) Porosity

The porosity of each tablet was determined using the following equation.

$$\text{Porosity} = \frac{\text{Volume of tablet} - \frac{\text{weight of tablet}}{\text{true density of ingredients}}}{\text{Volume of tablet}} \times 100$$

(2) Buccal Solubility

The time to complete dissolution by saliva in the oral cavity was determined in a healthy adult male volunteer (45 years old, body height 165 cm, body weight 55 kg). The test was performed in duplicate and the mean of the results of two determinations was adopted.

(3) Disintegration Time

The disintegration time of each tablet was determined in accordance with the disintegration test described in Japanese Phamacopoeia XII. The mean of results of six determinations was adopted.

(4) Hardness

The hardness of each tablet was measured with a tablet hardness tester (TH-100, Toyama Sangyo). The test was performed in 10 runs and the mean of results of 10 determinations was adopted.

(5) Falling Impact Strength

Each tablet was dropped from a height of 30 cm on a glass plate and the degree of destruction was measured. The test was performed in 10 replicates and the mean result was adopted.

TABLE 22-1

| | Example | | | | | | |
|---|---|---|---|---|---|---|---|
| | 1 | 2 | 3 | 4 | 5 | 6 | 7 |
| Buccal dissolution time (min.) | 0.8 | 0.5 | 0.6 | 0.3 | 0.5 | 1.2 | 1.2 |
| Disintegration time (min.) | 0.5 | 0.4 | 0.3 | 0.2 | 0.4 | 0.8 | 0.6 |
| Hardness (kg) | 14 | 5 | 7 | 7 | 10 | 16 | 12 |
| Falling impact strength (%) | 0 | 0 | 0 | 60 | 50 | 0 | 0 |
| Porosity (%) | 45 | 53 | 38 | 65 | 50 | 39 | 46 |
| Molding pressure (Kg/cm$^2$) | 32 | 38 | 34 | 10 | 32 | 32 | 32 |
| Water used (% (w/w)) | 1.6 | 2.0 | 2.0 | 1.6 | 0.5 | 5.0 | 1.8 |

TABLE 22-2

| | Example | | | | | | |
|---|---|---|---|---|---|---|---|
| | 8 | 9 | 10 | 11 | 12 | 13 | 14 |
| Buccal dissolution time (min.) | 1.0 | 0.8 | 0.8 | 1.4 | 1.2 | 1.1 | 1.5 |
| Disintegration time (min.) | 0.5 | 0.4 | 0.5 | 0.8 | 0.8 | 0.7 | 0.8 |
| Hardness (kg) | 10 | 10 | 10 | 14 | 12 | 8 | 13 |
| Falling impact strength (%) | 0 | 0 | 0 | 0 | 0 | 0 | 0 |
| Porosity (%) | 36 | 52 | 50 | 30 | 32 | 35 | 39 |
| Molding pressure (Kg/cm$^2$) | 36 | 101 | 127 | 38 | 35 | 29 | 32 |
| Water used (% (w/w)) | 2.0 | 0.9 | 1.1 | 1.4 | 1.2 | 1.0 | 1.2 |

TABLE 22-3

| | Example | | | | | | |
|---|---|---|---|---|---|---|---|
| | 15 | 16 | 17 | 18 | 19 | 20 | 21 |
| Buccal dissolution time (min.) | 1.0 | 1.2 | 1.3 | 1.0 | 0.7 | 0.8 | 0.8 |
| Disintegration time (min.) | 0.6 | 0.6 | 0.9 | 0.7 | 0.4 | 0.6 | 0.6 |
| Hardness (kg) | 10 | 12 | 14 | 10 | 8 | 12 | 10 |
| Falling impact strength (%) | 0 | 0 | 0 | 0 | 0 | 0 | 0 |
| Porosity (%) | 40 | 38 | 41 | 45 | 55 | 49 | 60 |
| Molding pressure (Kg/cm$^2$) | 30 | 32 | 29 | 25 | 25 | 32 | 25 |
| Water used (% (w/w)) | 1.5 | 1.5 | 2.0 | 1.2 | 1.0 | 0.8 | 1.2 |

TABLE 23

| | Reference Example | | | |
|---|---|---|---|---|
| | 1 | 2 | 3 | 4 |
| Buccal dissolution time (min.) | 12 | 8 | 12 | 2.5 |
| Disintegration time (min.) | 10 | 6 | 7 | 2.1 |
| Hardness (kg) | 19 | 8 | 11 | 8 |
| Falling impact strength (%) | 90 | 50 | 90 | 80 |
| Porosity (%) | 15 | 13 | 17 | 40 |
| Molding pressure (Kg/cm$^2$) | 1910 | 1980 | 1700 | 32 |
| Water used (% (w/w)) | 10 | 10 | 12 | 2 |

Comparison of Tables 22 and 23 indicate that the fast dissolving tablet of the present invention is superior in solubility and disintegratability and yet has an adequate mechanical strength.

What is claimed is:

1. A fast dissolving tablet which contains an effective amount of an active ingredient and a water-soluble carbohydrate, and having
    (1) a porosity of 30 to 70%,
    (2) a hardness of 3 to 20 kg, and
    (3) a falling impact strength of 0 to 70%, which tablet is produced from a composition to be compression-molded comprising said active ingredient, 30 to 80% by weight of said water-soluble carbohydrate having a mean particle size of 20 to 70 μm, and 1 to 3% by weight of water, said weights based on the composition to be compression-molded, by a process comprising the steps of adhering particles of said carbohydrate to each other by moistening the surfaces of said particles with said water in the composition, molding the composition at a pressure of 5 to 130 Kg/cm$^2$, and removing said water.

2. A fast dissolving tablet obtainable by compression-molding a composition comprising an active ingredient, 30 to 80% by weight of a water-soluble carbohydrate having a mean particle size of 20 to 70 μm and 1 to 3% by weight of water into a tablet form at a pressure of 5 to 130 Kg/cm$^2$ and drying the compression-molded tablet, said fast dissolving tablet having (1) a porosity of 30 to 70%, (2) a hardness of 3 to 20 kg, and (3) a falling impact strength of 0 to 70%.

3. A fast dissolving tablet according to claim 2 which has a porous structure with a porosity of 30 to 70%, a hardness of 3 to 20 kg and a disintegration time of 0.05 to 3.0 minutes.

4. A fast dissolving tablet according to claim 2 which has a porous structure with a porosity of 30 to 70%, a hardness of 3 to 20 kg, a disintegration time of 0.05 to 3.0 minutes, a falling impact strength of 0 to 70% and buccal solubility of 0.05 to 3.0 minutes.

5. A fast dissolving tablet according to claim 2 which contains 0.05 to 90% by weight of said active ingredient and 10 to 90% by weight of said carbohydrate.

6. A fast dissolving tablet according to claim 1 which contains at least one member selected from the group consisting of a vitamin, a crude drug, an antipyretic-analgesic-antiinflammatory agent, an antianxiety drug, a hypnotic-sedative agent, a stomach-digestive agent, an intestinal function-controlling agent, an antacid, an antitussive-expectorant, an antihypertensive drug, an antidiabetic agent, a drug for osteoporosis and a skeletal muscle relaxant as said active ingredient.

7. A fast dissolving tablet according to claim 2 which contains at leat one member selected from the group consisting of sugar, starch sugars, lactose, honey, sugar alcohols and tetroses as said carbohydrate.

8. A fast dissolving tablet according to claim 2 which contains at least one member of additives selected from the group consisting of disintegrators, binders, acids, foaming agents, artificial sweeteners, flavorants, lubricants and colorants.

9. A fast dissolving tablet according to claim 2 which contains an effective amount of said active ingredient, 10 to 90% by weight of water-soluble carbohydrate and has a porous structure with a porosity of 20 to 80%.

10. A fast dissolving tablet according to claim 9 which contains 0.1 to 10% by weight of said active ingredient and 50 to 85% by weight of said water-soluble carbohydrate.

11. A fast dissolving tablet according to claim 9 which contains 10 to 30% by weight of said active ingredient and 30 to 80% by weight of said water-soluble carbohydrate.

12. A fast dissolving tablet according to claim 9 which contains 30 to 70% by weight of said active ingredient and 15 to 75% by weight of said water-soluble carbohydrate.

13. A fast dissolving tablet according to claim 2 obtainable by compression-molding a composition comprising an effective amount of said active ingredient, water-soluble carbohydrate and 0.3 to 7% by weight of water into a tablet form at a pressure of 5 to 130 $Kg/cm^2$ and drying the resulting tablet.

* * * * *